(12) United States Patent
Swartz et al.

(10) Patent No.: US 6,168,931 B1
(45) Date of Patent: Jan. 2, 2001

(54) ENHANCED IN VITRO SYNTHESIS OF BIOLOGICAL MACROMOLECULES USING A NOVEL ATP REGENERATION SYSTEM

(75) Inventors: James R. Swartz, Menlo Park; Dong-Myung Kim, Palo Alto, both of CA (US)

(73) Assignee: The Board of Trustees of the Leland Stanford Junior University, Palo Alto, CA (US)

( * ) Notice: Under 35 U.S.C. 154(b), the term of this patent shall be extended for 0 days.

(21) Appl. No.: 09/270,814

(22) Filed: Mar. 17, 1999

(51) Int. Cl.$^7$ .................................................. C12P 21/06
(52) U.S. Cl. ............................................................. 435/68.1
(58) Field of Search ............................................. 435/68.1

(56) References Cited

U.S. PATENT DOCUMENTS

| | | | |
|---|---|---|---|
| 4,668,624 | 5/1987 | Roberts | 435/68 |
| 5,324,637 | 6/1994 | Thompson et al. | 435/68.1 |
| 5,478,730 | 12/1995 | Alakhov et al. | 435/68.1 |
| 5,556,769 | 9/1996 | Wu et al. | 435/69.1 |
| 5,593,856 | 1/1997 | Choi et al. | 435/68.1 |
| 5,895,753 | 4/1999 | Mierendorf et al. | 435/68.1 |

OTHER PUBLICATIONS

Kawarasaki, Yasuaki, et al., "A Long–Lived Batch Reaction System Of Cell–Free Protein Synthesis[1]" *Analytical Biochemistry* (1995) vol. 226:320–324.

Kigawa, Takanori, et al., "A Continuous Cell–Free Protein Synthesis System For Coupled Transcription–Translation[1]" *J. Biochem.* (1991) vol. 110:166–168.

Kim, Dong–Myung, et al., "A Semicontinuous Prokaryotic Coupled Transcription/Translation System Using A Dialysis Membrane," *Biotechnol Prog.* (1996) vol. 12:645–649.

Kim, Dong–Myung, et al., "A Highly Efficient Cell–Free Synthesis From *Escherichia Coli*," *Eur. J. Biochem.* (1996) vol. 239:881–886.

Kudlicki, Wieslaw, et al., "High Efficiency Cell–Free Synthesis Of Proteins: Refinement Of The Coupled Transcription/Translation System," *Analytical Biochem.* (1992) vol. 206:389–393.

Muller, Yves A., et al., "Structure Of The Thiamine–And Flavin–Dependent Enzyme Pyruvate Oxidase," *Science* (Feb. 12, 1993) vol. 259:965–967.

Nakano, Hideo, et al., "Highly Productive Cell–Free Protein Synthesis System Using Condensed Wheat–Germ Extract," *Journal Of Biotechnology* (1996) vol. 46:275–282.

(List continued on next page.)

*Primary Examiner*—Ponnathapu Achutamurthy
*Assistant Examiner*—Kathleen Kerr
(74) *Attorney, Agent, or Firm*—Pamela J. Sherwood; Bozicevic, Field, & Francis

(57) ABSTRACT

Compositions and methods are provided for the enhanced in vitro synthesis of biological molecules where ATP is required for synthesis. Of particular interest is the synthesis of polymers, e.g. nucleic acids, polypeptides, and complex carbohydrates. A homeostatic system is used for production of ATP, where the required high energy phosphate bonds are generated in situ, e.g. through coupling with an oxidation reaction. The homeostatic energy source will typically lack high energy phosphate bonds itself, and will therefore utilize free phosphate in the reaction mix during generation of ATP. Since inorganic phosphate can be an inhibitory by-product of synthesis, the period of time when synthesis is maintained in vitro can be extended. The homeostatic energy source is provided in combination with an enzyme that catalyzes the creation of high energy phosphate bonds and with an enzyme that can use that high energy phosphate bond to regenerate ATP.

12 Claims, 8 Drawing Sheets

OTHER PUBLICATIONS

Noren, Christopher J., et al., "A General Method For Site–Specific Incorporation Of Unnatural Amino Acids Into Proteins," *Science* (Apr. 14, 1989) vol. 244:182–188.

Patnaik, Ranjan, et al., "*E–Coli*–Based In Vitro Transcription/Translation: In Vivo–Specific Synthesis Rates And High Yields In A Batch System," *BioTechniques* (1998) vol. 24, No. (5):862–868.

Ryabova, Lyubov A., et al., "Acetyl Phosphate As An Energy Source For Bacterial Cell–Free Translation Systems," *Analytical Biochemistry* (1995) vol. 226:184–186.

Spirin, Alexander S., et al., "A Continuous Cell–Free Translation System Capable Of Producing Polypeptides In High Yield," *Science* (Nov. 25, 1988) vol. 242:1162–1164.

Crans et al. Enzymatic Regeneration of ATP in Methods in Enzymology (1987) 136:263–280, 1987.*

Langer et al. Enzymatic Regeneration of ATP. AIChE Journal (1976) 22(6):1079–1090, 1987.*

Snyder et al., (May 15,1991), "Effects of Polyamine Analogs on the Extent Fidelity on In vitro Polypeptide Synthesis-"*Biochemical and Biophysical Research oCommunications*, vol.176(3):1383–1392.

* cited by examiner

ENHANCED IN VITRO SYNTHESIS OF BIOLOGICAL MACROMOLECULES USING A NOVEL ATP REGENERATION SYSTEM

BACKGROUND OF THE INVENTION

The directed synthesis of proteins and other biological macromolecules is one of the great achievements of biochemistry. The development of recombinant DNA techniques has allowed the characterization and synthesis of highly purified coding sequences, which in turn can be used to produce highly purified proteins, even though in native cells the protein may be available only in trace amounts. Polypeptide chains can be synthesized by chemical or biological processes. The biological synthesis may be performed within the environment of a cell, or using cellular extracts and coding sequences to synthesize proteins in vitro.

For several decades, in vitro protein synthesis has served as an effective tool for lab-scale expression of cloned or synthesized genetic materials. In recent years, in vitro protein synthesis systems have been considered as an alternative to conventional recombinant DNA technology, because of disadvantages associated with cellular expression. In vivo, proteins can be degraded or modified by several enzymes synthesized with the growth of the cell, and after synthesis may be modified by post-translational processing, such as glycosylation, deamination or oxidation. In addition, many products inhibit metabolic processes and their synthesis must compete with other cellular process required to reproduce the cell and to protect its genetic information.

Because it is essentially free from cellular regulation of gene expression, in vitro protein synthesis has advantages in the production of cytotoxic, unstable, or insoluble proteins. The over-production of protein beyond a predetermined concentration can be difficult to obtain in vivo, because the expression levels are regulated by the concentration of product. The concentration of protein accumulated in the cell generally affects the viability of the cell, so that over-production of the desired protein is difficult to obtain. In an isolation and purification process, many kinds of protein are insoluble or unstable, and are either degraded by intracellular proteases or aggregate in inclusion bodies, so that the loss rate is high.

In vitro synthesis circumvents many of these problems. Also, through simultaneous and rapid expression of various proteins in a multiplexed configuration, this technology can provide a valuable tool for development of combinatorial arrays for research, and for screening of proteins. In addition, various kinds of unnatural amino acids can be efficiently incorporated into proteins for specific purposes (Noren et al. (1989) Science 244:182–188). However, despite all its promising aspects, the in vitro system has not been widely accepted as a practical alternative, mainly due to the short reaction period, which causes a poor yield of protein synthesis.

The development of a continuous flow in vitro protein synthesis system by Spirin et al (1988) Science 242:1162–1164 proved that the reaction could be extended up to several hours. Since then, numerous groups have reproduced and improved this system (Kigawa et al. (1991) J. Biochem. 110:166–168; Endo et al. (1992) J. Biotechnol. 25:221–230. Recently, Kim and Choi (1996) Biotechnol. Prog. 12: 645–649, reported that the merits of batch and continuous flow systems could be combined by adopting a 'semicontinuous operation' using a simple dialysis membrane reactor. They were able to reproduce the extended reaction period of the continuous flow system while maintaining the initial rate of a conventional batch system. However, both the continuous and semi-continuous approaches require quantities of expensive reagents, which must be increased by a significantly greater factor than the increase in product yield.

Several improvements have been made in the conventional batch system (Kim et al. (1996) Eur. J. Biochem. 239: 881–886; Kuldlicki et al. (1992) Anal. Biochem. 206:389–393; Kawarasaki et al (1995) Anal. Biochem. 226: 320–324). Although the semicontinuous system maintains the initial rate of protein synthesis over extended periods, the conventional batch system still offers several advantages, e.g. convenience of operation, easy scale-up, lower reagent costs and excellent reproducibility. Also, the batch system can be readily conducted in multiplexed formats to express various genetic materials simultaneously.

Most recently, Patnaik and Swartz (1998) Biotechniques 24:862–868 reported that the initial specific rate of protein synthesis could be enhanced to a level similar to that of in vivo expression through extensive optimization of reaction conditions. It is notable that they achieved such a high rate of protein synthesis using the conventional cell extract prepared without any condensation steps (Nakano et al. (1996) J. Biotechnol. 46:275–282; Kim et al. (1996) Eur. J. Biochem. 239:881–886). Their result implies that further improvement of the batch system, especially in terms of the longevity of the protein synthesis reaction, would substantially increase the productivity for batch in vitro protein synthesis. However, the reason for the early halt of protein synthesis in the conventional batch system has remained unclear.

As shown from the above, both protein productivity and production amount are still low, which is an obstacle in implementing the industrialization of cell-free protein synthesis. Therefore, improvements are greatly required in terms of the total productivity of the protein by increasing the specific production rate and the length of system operation, and in terms of a cost-reduction by regenerating an expensive energy source in order to recycle the regenerated energy source. It has been suggested that accumulation of small molecular weight by-products could inhibit protein synthesis. The continuous removal of the inhibitory by-product(s) as well as the continuous supply of substrates for protein synthesis may enable the continuous or semi-continuous reaction system to support protein synthesis over long reaction periods. Elucidation of inhibitory products, and prevention of their synthesis is of great interest for development of in vitro synthetic systems.

SUMMARY OF THE INVENTION

Compositions and methods are provided for the enhanced in vitro synthesis of biological molecules where ATP is required for synthesis. Of particular interest is the synthesis of polymers, e.g. nucleic acids, polypeptides, and complex carbohydrates. A homeostatic system is used for production of ATP, where use of this energy system prevents a net increase in free phosphate as a result of ATP hydrolysis. The phosphate that is released from ATP hydrolysis is recycled into high energy phosphate bonds, thereby preventing its accumulation. Energy homeostasis is accomplished by addition of a regenerative energy source, e.g. pyruvate in combination with the enzyme pyruvate oxidase to generate acetyl phosphate. In a preferred embodiment, energy sources such as phosphoenol pyruvate, which increase the net free phosphate in the reaction mix, are omitted.

Relevant literature

Muller et al. (1993) *Science* 259:965–967 describes the structure of the thiamine- and flavin-dependent enzyme, pyruvate oxidase. Ryabova et al. (1995) *Anal. Biochem.* 226:184–186 describe the use of acetyl phosphate as an energy source for bacterial cell-free translation systems. Pyruvate oxidase mutants are described in U.S. Pat. No. 5,153,138, and pyruvate oxidase is further described in U.S. Pat. Nos. 4,666,832 and 4,246,342.

BRIEF DESCRIPTION OF THE DRAWINGS

FIG. 1A depicts a conventional scheme using phosphoenol pyruvate (PEP) and pyruvate kinase (PK); FIG. 1B depicts the use of pyruvate, pyruvate oxidase (Pox) and endogenous acetyl kinase (AcK).

DETAILED DESCRIPTION OF THE EMBODIMENTS

Compositions and methods are provided for the enhanced in vitro synthesis of biological molecules where ATP is required for synthesis. Of particular interest is the synthesis of polymers, e.g. nucleic acids, polypeptides, and complex carbohydrates. A homeostatic system is used for production of ATP, where use of this energy system prevents a net increase in free phosphate as a result of ATP hydrolysis. The phosphate that is released from ATP hydrolysis is recycled into the energy pool, thereby preventing its accumulation.

The primary source of energy for most biological synthesis is ATP. ATP is generated from ADP and a secondary source of high energy phosphate bonds, e.g. phosphoenol pyruvate (PEP), creatine phosphate, or acetyl phosphate. These chemicals recharge ADP into ATP by catalysis with the enzymes pyruvate kinase, creatine kinase, and acetate kinase, respectively. In addition, there are some reports regarding the use of polyphosphate to recycle ATP. Energy homeostasis is accomplished by addition of a secondary energy source that indirectly provides high energy phosphate bonds without release of free phosphate.

Figure 1A:
FIGS. 1A and 1B are flow diagrams illustrating regeneration of ATP in an in vitro protein synthesis system.
Figure 1B:
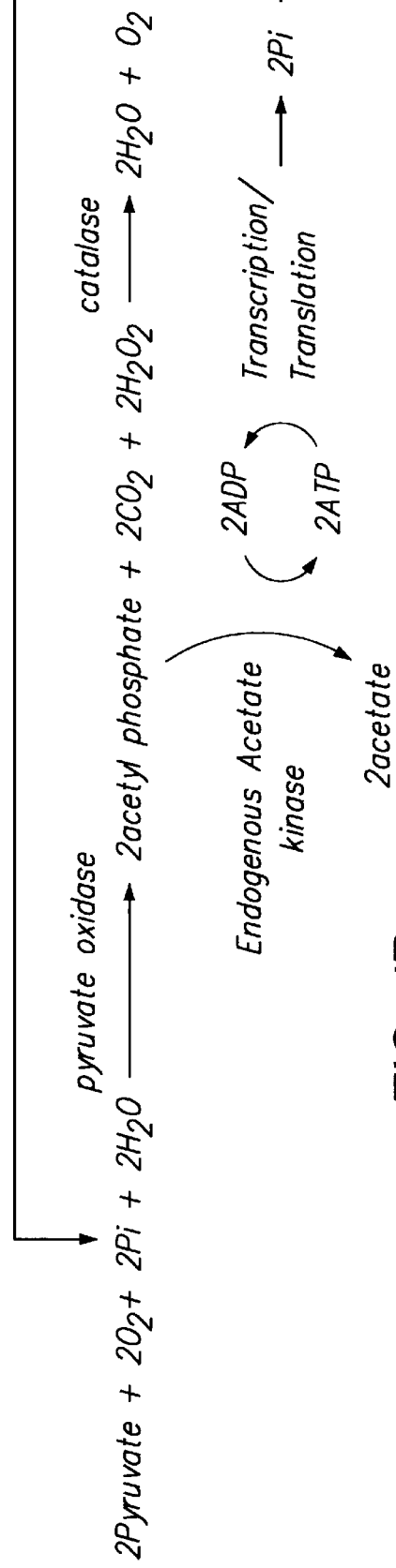

Exemplary is the use of pyruvate in combination with the enzyme pyruvate oxidase as the homeostatic energy source. During oxidation of pyruvate, acetyl phosphate is generated, which then directly regenerates ATP from ADP. The metabolic pathway is shown in FIG. 1B. The phosphate that is hydrolyzed from ATP is recycled during the pyruvate oxidation to generate acetyl phosphate, thereby preventing a net accumulation of free phosphate, which can have an inhibitory effect on synthetic reactions. The reaction mix may comprise small amounts of secondary energy sources that result in free phosphate accumulation, e.g. acetyl phosphate, PEP, creatine phosphate, but at a significantly lower concentration than with previously described in vitro synthesis reactions.

While the present invention has been described primarily in terms of synthetic reactions, one of skill in the art will appreciate the use of the subject homeostatic energy system in other in vitro reactions. For example, protein folding and protein transport require the use of ATP, and may benefit from the subject methods.

DEFINITIONS

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Homeostatic energy source, as used herein, refers to a secondary source of energy for driving in vitro synthetic reactions utilizing ATP as a primary energy source, whereby the free phosphate generated by ATP hydrolysis is recycled. Instead of exogenous addition of a source of high energy phosphate bonds, the required high energy phosphate bonds are generated in situ, e.g. through coupling with an oxidation reaction. The homeostatic energy source will typically lack high energy phosphate bonds itself, and will therefore utilize free phosphate present in the reaction mix during ATP regeneration. Since inorganic phosphate can be an inhibitory by-product of synthesis, the period of time when synthesis is maintained in vitro can be extended. The homeostatic energy source is provided in combination with an enzyme that catalyzes the creation of high energy phosphate bonds.

In one embodiment of the invention, the homeostatic energy source is pyruvate, which may be supplied as a suitable biologically acceptable salt, or as the free acid, pyruvic acid. The final concentration of pyruvate at initiation of synthesis will usually be at least about 1 mM, more usually at least about 10 mM, and not more than about 500 mM, usually not more than about 100 mM. Additional pyruvate may be added to the reaction mix during the course of synthesis to provide for longer reaction times.

Preferably, secondary energy sources that result in the net accumulation of free phosphate, including creatine phosphate, polyphosphate, acetyl phosphate and phosphoenol pyruvate, are not added to the reaction mix at a significant concentration. The concentration of such energy sources in the reaction mix at the initiation of synthesis will generally be less than about 10 mM, more usually less than about 1 mM, and may be less than about 0.5 mM. Excluded from such energy sources is ATP itself, which will be included in the reaction mix at conventional concentrations as a primary energy source.

Regenerative enzyme: as herein refers to an enzyme that regenerates a high energy phosphate bond from free phosphate and the homeostatic energy source, where the free phosphate may be recycled from hydrolysis of ATP. Where the homeostatic energy source is pyruvate, the enzyme will catalyze the formation of acetyl phosphate from pyruvate, as shown in FIG. 1B. Since acetyl phosphate can be used as an energy source for synthesis, the pyruvate oxidase reaction provides the basis for regeneration of ATP that has been hydrolyzed in the process of protein synthesis.

An exemplary regenerative enzyme is pyruvate oxidase, EC 1.2.3.3.; CAS: 9001-96-1. It is known that pyruvate oxidase is produced by a variety of microorganisms. For example, it is known to be produced by *Lactobacillus delbrueckii, Lactobacillus plantarum*, microorganisms of the genus Pediococcus, Streptococcus, and Aerococcus, microorganisms of the genus Leuconostoc, etc.

The reaction mix will comprise a concentration of regenerative enzyme sufficient to maintain the ATP pool, usually at least about 0.1 U/ml, more usually at least about 1 U/ml, and preferably at least about 5 U/ml, where the unit definition is that one unit will produce 1.0 $\mu$mole of $H_2O_2$ per minute during the conversion of pyruvate and phosphate to acetylphosphate and $CO_2$. It will be understood by one of skill in the art that higher concentration may be present, although generally at less than about 1000 U/ml.

The regenerative enzyme may be provided for in the reaction mix in a variety of ways. Purified or semi-purified enzyme may be added to the reaction mix Commercial preparations of pyruvate oxidase are available, or the enzyme may be purified from natural or recombinant sources according to conventional methods. The genetic sequences of pyruvate oxidases may be used as a source of recombinant forms of the enzyme, for example see Muller et al., supra.; Pellerberg et al. (1996) *Mol. Microbiol.* 19:803–813; Zhou et al., Genbank accession number 3818594, etc.

The enzyme may also be included in the extracts used for synthesis. For example, extracts can be derived from *E. coli* for protein synthesis. The *E. coli* used for production of the extracts may be genetically modified to encode a suitable pyruvate oxidase. Alternatively, where the synthetic reactions are protein synthesis, a template, e.g. mRNA encoding pyruvate oxidase, plasmid comprising a suitable expression construct of pyruvate oxidase, etc. may be spiked into the reaction mix, such that a suitable amount of pyruvate oxidase is produced during synthesis.

In vitro synthesis: as used herein refers to the cell-free synthesis of biological macromolecules in a reaction mix comprising biological extracts and/or defined reagents. The reaction mix will comprise at least ATP, a homeostatic energy source and regenerative enzyme; a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Also included are enzyme(s) that catalyze the regeneration of ATP from high energy phosphate bonds, e.g. acetate kinase, creatine kinase, etc. Such enzymes may be present in the extracts used for translation, or may be added to the reaction mix. Such synthetic reaction systems are well-known in the art, and have been described in the literature.

The cell free synthesis reaction may be performed as batch, continuous flow, or semi-continuous flow, as known in the art.

METHODS FOR ENHANCED IN VITRO SYNTHESIS

The subject energy producing system is useful for in vitro reactions that utilize ATP as a primary energy source, particularly where the accumulation of free phosphate is inhibitory to the reaction. Synthetic reactions are of particular interest, but the methods are also applicable to such in vitro systems as protein folding, protein transport, etc.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include wheat germ extracts (Roberts et al. (1973) *P.N.A.S.* 70:2330), reticulocyte extracts (Pelham et al. (1976) *Eur. J. Biochem.* 67:247), *E. coli* extracts, etc., which can be treated with a suitable nuclease to eliminate active endogenous mRNA.

In addition to the above components such as cell-free extract, genetic template, amino acids and energy sources, materials specifically required for protein synthesis may be added to the reaction. These materials include salt, polymeric compounds, cyclic AMP, inhibitors for protein or nucleic acid degrading enzymes, inhibitor or regulator of protein synthesis, oxidation/reduction adjuster, non-denaturing surfactant, buffer component, spermine, spermidine, etc.

The salts preferably include potassium, magnesium, ammonium and manganese salt of acetic acid or sulfuric acid, and some of these may have amino acids as a counter anion. The polymeric compounds may be polyethylene glycol, dextran, diethyl aminoethyl, quaternary aminoethyl and aminoethyl. The oxidation/reduction adjuster may be dithiothreitol, ascorbic acid, glutathione and/or their oxides. Also, a non-denaturing surfactant such as Triton X-100 may be used at a concentration of 0–0.5 M. Spermine and spermidine may be used for improving protein synthetic ability, and cAMP may be used as a gene expression regulator.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5–10 and a temperature of 20°–50° C., and more preferably, in the range of pH 6–9 and a temperature of 25°–40° C.

When using a protein isolating means in a continuous operation mode, the product output from the reactor through a membrane flows into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine or $^3$H-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

Protein Synthesis using Pyruvate as Energy Source

A new approach for the regeneration of ATP during cell-free protein synthesis was developed to prolong the synthesis reaction, by avoiding the accumulation of inorganic phosphate. This approach is demonstrated in a batch system derived from *Escherichia coli*. Contrary to the conventional methods in which exogenous energy sources contain high-energy phosphate bonds, the new system was designed to continuously generate the required high-energy phosphate bonds within the reaction mixture, thereby recycling the phosphate released during protein synthesis. If allowed to accumulate, phosphate inhibits protein synthesis, most likely by reducing the concentration of free magnesium ion.

*Pediococcus sp.* pyruvate oxidase, when introduced in the reaction mixture along with thiamine pyrophosphate (TPP); and flavin adenine dinucleotide (FAD), catalyzed the generation of acetyl phosphate from pyruvate and inorganic phosphate. Acetyl kinase, already present with sufficient activity in *Escherichia coli* S30 extract, then catalyzed the regeneration of ATP. Oxygen is required for the generation of acetyl phosphate and the $H_2O_2$ produced as a by-product is sufficiently degraded by endogenous catalase activity.

Through the continuous supply of chemical energy, and also through the prevention of inorganic phosphate accumulation the duration of protein synthesis was extended to 2.5 hours. Protein accumulation levels also increased. The synthesis of human lymphotoxin benefits more than that of chloramphenicol acetyl transferase (CAT) since the former is more sensitive to phosphate inhibition. In the expression of CAT, although the initial rate of protein synthesis in the new system was significantly lower than with the conventional system, remarkable improvement in the longevity of the reaction made the protein synthesis yield comparable to the conventional system using phosphoenol pyruvate (PEP).

The benefits of the present system are most striking in the expression of certain proteins particularly sensitive to the concentrations of inorganic phosphate and magnesium. In the case of human lymphotoxin (hLT), whose expression level was strongly dependent on the concentrations of inorganic phosphate and magnesium, the final yield after a 3 hour incubation reached 1.5 times that of the conventional reaction using PEP.

Material and Methods

Phosphoenol pyruvate (PEP) and E.coli total tRNA mixture were purchased from Boerhinger-Mannheim (Indianapolis, Ind.). L-[U-$^{14}$C] leucine (11.7 GBq/mmol), L-[U-$^{3}$H] leucine (4.14 TBq/mmol) and [5,6-$^{3}$H] UTP were from Amersham Pharmacia Biotechnology (Uppsala, Sweden). All the other reagents were obtained from Sigma (St.Louis, Mo.). T7 RNA polymerase was prepared from the culture of E.coli strain BL21(pAR1219) according to the procedures of Davanloo et al. (1984) Proc. Natl. Acad. Sci. U.S.A. 81: 2035–2039. Plasmid pK7CAT, which includes the bacterial CAT sequence between the T7 promoter and T7 terminator (Kigawa et al. (1995) Journal of Biomolecular NMR 6(2):129–134) was used as a template for CAT synthesis. For hLT synthesis, plasmid pK7LT was constructed by replacing the CAT sequence of pK7CAT with the human lymphotoxin sequence. S30 extract was prepared from E.coli K12 (strain A19) as described earlier (Kim et al. (1996b), supra.)

The standard reaction mixture consists of the following components: 57 mM Hepes-KOH (pH8.2),1.2 mM ATP, 0.85 mM each of GTP, UTP and CTP, 1 mM DTT, 0.64 mM CAMP, 200 mM potassium glutamate, 80 mM NH$_4$(OAc), 15 mM Mg(OAc)$_2$, 34 mg/ml folinic acid, 6.7 μg/ml plasmid, 33 μg/ml T7RNA polymerase, 500 μM each of 20 unlabeled amino acids and [$^{14}$C] leucine (11.0 μM) or [$^{3}$H] leucine (1.2 μM), 2% PEG 8000, 32 mM PEP, and 0.24 volume of S30 extract. In reactions in which pyruvate was used as the energy regenerating compound, PEP was removed from the standard reaction mixture and 32 mM pyruvate, 6 U/ml pyruvate oxidase, 6.7 mM potassium phosphate, 3.3 mM TPP, and 0.3 mM FAD were added. Reactions were run for given time periods in 15 to 60 μl volumes in a waterbath set at 37° C.

The amount of synthesized protein was estimated from the measured TCA-insoluble radioactivities as described earlier (Kim et al., 1996a, supra.) Radioactivities of samples were measured in a liquid scintillation counter (Beckman LS3801). For SDS-PAGE analysis, samples were loaded on a 16% SDS-PAGE gel (NOVEX) with $^{14}$C standard markers (Amersham). Kodak XOMAT film was exposed to a dried gel overnight and developed in an automatic X-ray film developer.

Change of mRNA concentration during the incubation was monitored by measuring the TCA-insoluble radioactivity of samples from reactions containing [$^{3}$H]-UTP following the same procedures used for estimation of protein synthesis except that the NaOH-hydrolysis step was omitted.

Quantitative analysis of inorganic phosphate was carried out according to the procedures of Saheki et al. (1985) Anal. Biochem. 148:277–281 after minor modifications. 2 μl samples were taken and mixed with 15 μl of 20% SDS solution and 43 μl water. After sequential addition of 670 μl solution A (100 mM zinc acetate, 15 mM ammonium molybdate, pH 5.0) and 170 μl solution B (10% ascorbic acid), each tube was incubated in a 30° C. gyratory incubator for 15 min. Finally, the concentration of inorganic phosphate was estimated from the measured OD$_{850}$ of sample and standard curve.

Results

Figure 2:
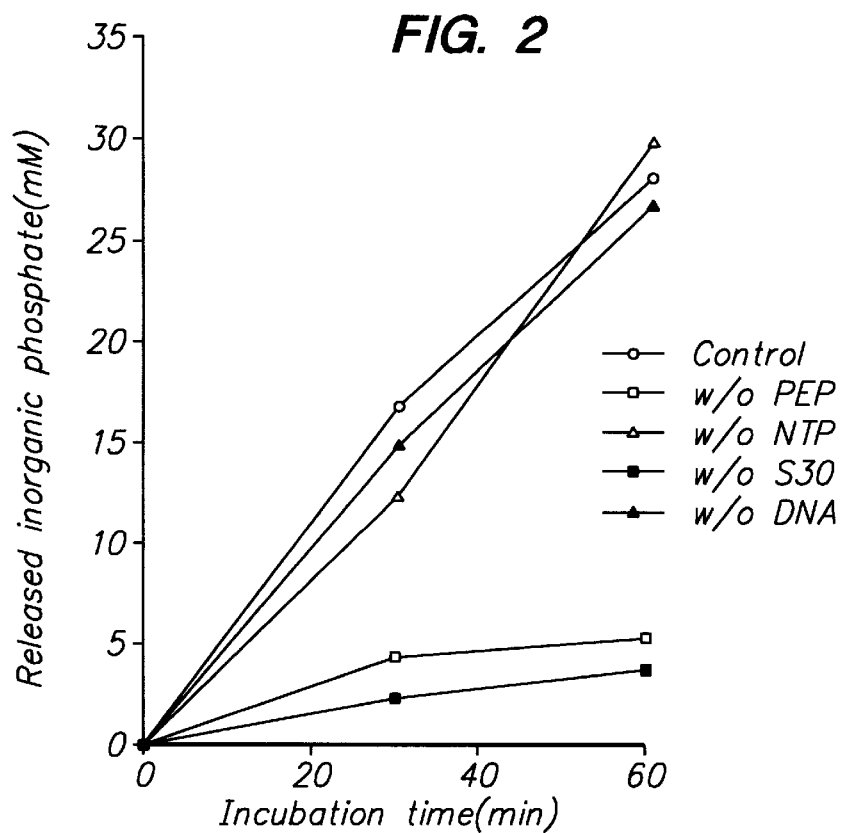
FIG. 2 is a graph showing accumulation of inorganic phosphate in the reaction mixture under various conditions.

Non-productive degradation of PEP. The concentration of inorganic phosphate in the standard reaction mixture initially containing 32 mM PEP was measured throughout the reaction period of protein synthesis. A standard reaction mixture (control) and reaction mixtures devoid of the indicated components (FIG. 2) were prepared and incubated. 2 μl samples were taken at given time points and the concentration of inorganic phosphate was measured as described in Material and Methods. As shown in FIG. 2, the concentration of inorganic phosphate in the reaction mixture increased linearly during the incubation period.

The accumulation of inorganic phosphate took place at the same rate even without addition of plasmid to the reaction mixture, demonstrating that the generation of phosphate occurs at the same rate in the absence of significant protein synthesis. The background level of protein synthesis due to contaminating mRNA and chromosomal DNA is negligible in our system, since the CPM value of a negative control reaction without plasmid DNA was less than 10% of a reaction programmed with pK7CAT.

The non-productive degradation of organic phosphate compounds reduces the amount of PEP available for ATP regeneration and protein synthesis and also increases the accumulation of phosphate. Without S30 extract in the incubation mixture, the accumulation of inorganic phosphate was negligible, suggesting that phosphate accumulation is catalyzed by phosphatase activity present in the S30 extract and is not the result of a spontaneous degradation of organic phosphate compounds (FIG. 2).

After a 60 min incubation, the concentration of inorganic phosphate in the reaction mixture reached 28 mM. As the maximal concentration of inorganic phosphate that can be directly generated from nucleotide triphosphates is only 7.6 mM (2.4 mM from ATP and 5.1 mM from other nucleotide triphosphates), it was clear that a significant amount of PEP was consumed either through direct degradation by phosphatase(s) or by recharging hydrolyzed nucleotide phosphates.

Comparison of inorganic phosphate concentrations in the incubations with or without PEP confirmed that the inorganic phosphate liberation into the reaction mixture was strongly dependent upon the presence of PEP (FIG. 2). Furthermore, neither the final concentration or production rate of inorganic phosphate in the reaction were significantly reduced even when all four nucleotides were removed from the reaction mixture. These results suggest that PEP is a major target of phosphatases and that uncoupled PEP hydrolysis can significantly reduce protein synthesis yields. In fact, the above results indicate that for a 30 minute protein synthesis reaction, as much as 50% of the energy source can be wasted. This will limit ATP regeneration and could explain, at least in part, the early halt of the in vitro protein synthesis reaction. However, subsequent PEP addition did not elongate the reaction period significantly. We then focused on the accumulation of inorganic phosphate in the reaction mixture, which could inhibit protein synthesis, most likely through chelation of free magnesium ion.

EXAMPLE 2

Use of Pyruvate As Energy Source With Phosphate Recycle

Besides PEP, creatine phosphate and acetyl phosphate have been successfully used as energy sources in various in vitro protein synthesis systems of eukaryotic and prokaryotic origins. Both of these substrates supported protein synthesis in our system as efficiently as PEP. However, similar to PEP, they lose their high-energy phosphate bond during the incubation with S30 extract. Thus, it appears that as long as one relies on the direct use of phosphate bond energy sources to regenerate ATP, the non-productive depletion of the energy source and accumulation of inorganic phosphate is almost inevitable. To attain an extended reaction period in the batch system, the present invention provides a system that does not require a high concentration of compounds with high-energy phosphate bonds, in other words, a system that can regenerate the high-energy phosphate donor in situ as well as ATP.

Pyruvate oxidase (E.C.1.2.3.3) plays an important role in the aerobic growth of lactobacteria by catalyzing the oxidative decarboxylation of pyruvate in several steps. Importantly, in the presence of the cofactors, TPP and FAD, this enzyme catalyzes the condensation of pyruvate and inorganic phosphate to generate acetyl phosphate, which can serve as an energy source in our in vitro protein synthesis system. This reaction was tested to see if acetyl phosphate could be continuously provided while avoiding the accumulation of inorganic phosphate. The inorganic phosphate produced either from protein synthesis or by degradation of acetyl phosphate would be recycled to generate another molecule of acetyl phosphate. The acetyl phosphate would, in turn, regenerate the required ATP. A simplified diagram for this strategy is depicted in FIG. 1B. In addition, since both acetyl phosphate and ATP are continually generated and depleted, the peak concentration of both is likely to be kept low enough to discourage non-productive hydrolysis.

Figure 3A:
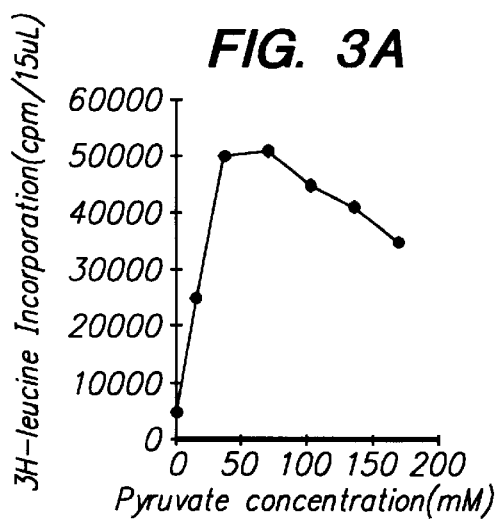
FIG. 3 is a graph depicting the use of pyruvate as energy source for protein synthesis.
Figure 3B:
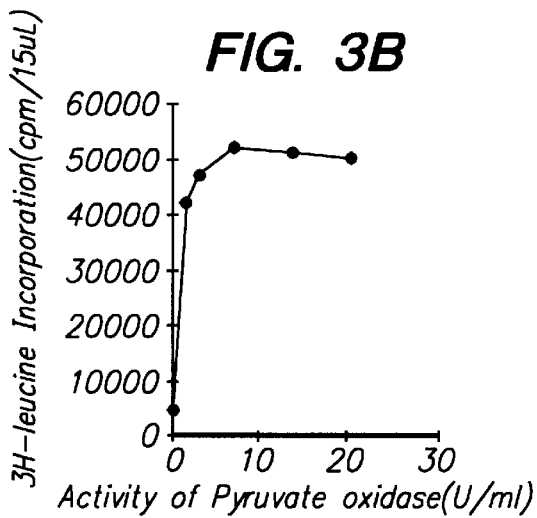
Figure 3C:
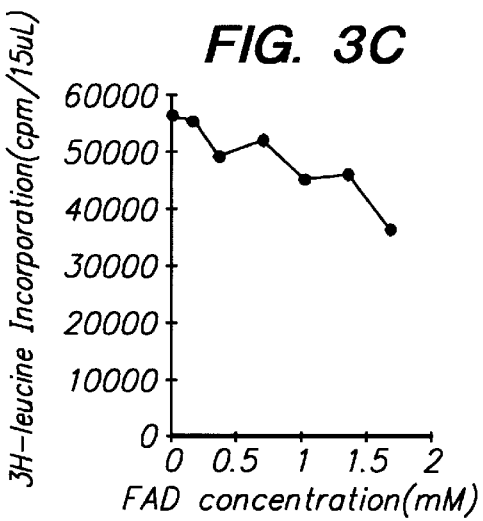
Figure 3D:
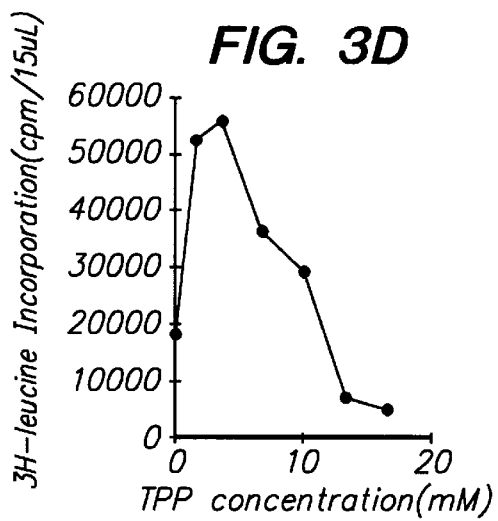
Figure 3E:
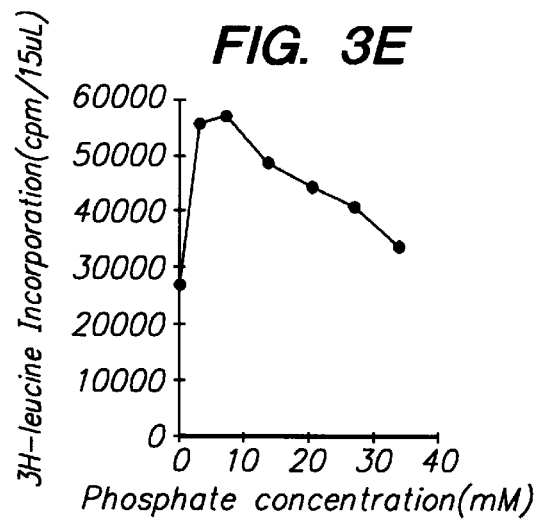

Expression of CAT in the pyruvate oxidase system. To examine this scheme under the reaction conditions for in vitro protein synthesis, the required compounds were introduced into the reaction mixture at different concentrations and incubated at 37° C. for one hour. Standard reaction mixtures containing different concentrations of pyruvate, pyruvate oxidase, FAD, TPP, and inorganic phosphate were prepared and incubated for an hour. The final amount of [$^3$H] leucine incorporation was measured as described in Materials and Methods. FIG. 3A; 6.7 U/ml pyruvate oxidase, 0.3 mM FAD, 3.3 mM TPP, 6.7 mM inorganic phosphate. FIG. 3B; 32 mM pyruvate, 0.3 mM FAD, 3.3 mM TPP, 6.7 mM inorganic phosphate. FIG. 3C; 32 mM pyruvate, 6.7 U/ml pyruvate oxidase, 3.3 mM TPP, 6.7 mM inorganic phosphate. FIG. 3D; 32 mM pyruvate, 6.7 U/ml pyruvate oxidase, 0.3 mM FAD, 6.7 mM inorganic phosphate. FIG. 3E; 32 mM pyruvate, 6.7 U/ml pyruvate oxidase, , 3.3 mM TPP, 0.3 mM FAD.

As shown in FIGS. 3A to 3E, TCA precipitable radioactivity demonstrates that the new strategy for ATP regeneration does support CAT synthesis. Initially, the final amount of synthesized protein was lower when compared with a control reaction using PEP. The amount of synthesized CAT increased with increasing concentrations of exogenous pyruvate oxidase and leveled off at 6.6 U/ml pyruvate oxidase. While relatively insensitive to the concentration of FAD, the yield of protein synthesis responded sharply to the concentrations of TPP and inorganic phosphate giving maximal protein synthesis at 3.3 mM and 6.6 mM respectively. The yield of protein synthesis was almost negligible when pyruvate oxidase was removed from the reaction mixture.

Figure 4:
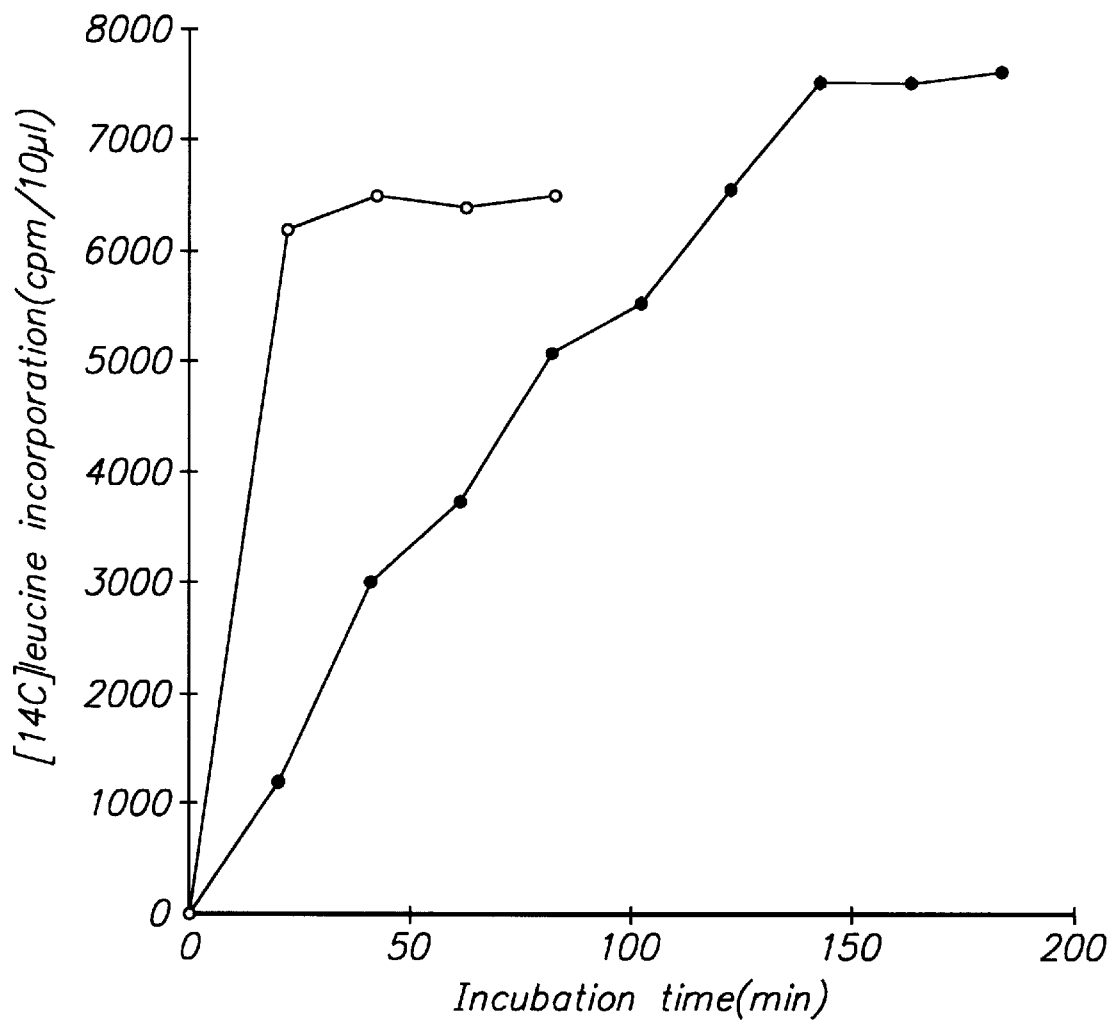
FIG. 4 is a time course of CAT synthesis in the conventional system using PEP (open circles) and using pyruvate (closed circles).

120 μl reaction mixtures of each system were prepared and incubated in 37° C. waterbath. 10 μl samples were withdrawn every 30 minutes and the [$^{14}$C] leucine-labeled radioactivity of protein was measured as described in materials and methods. After a one hour incubation, the final amount of synthesized protein reached at only 50% of that with the PEP reaction. We examined the time course of protein synthesis in this new system and compared it with the PEP system. Strikingly, as shown in FIG. 4, the initial rate of protein synthesis in the pyruvate system was maintained for over 2 hours, while the reaction with PEP slowed significantly after 20 minutes. As a result, despite the reduced initial rate of protein synthesis, the new system was able to produce protein at a volumetric yield comparable to the conventional system using PEP.

Figure 5:
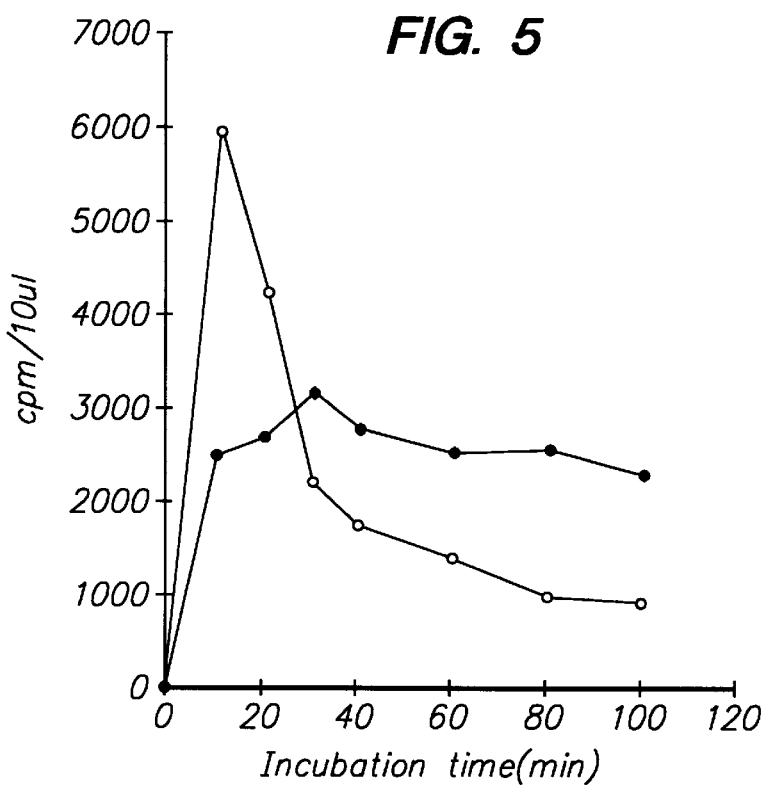
FIG. 5 is a time course of CAT mRNA concentration during the incubation of PEP(open circle) and pyruvate (closed circle).

The prolonged protein synthesis period was accompanied by a prolonged maintenance of mRNA level. Measurement of radioactivity from [$^3$H]-UTP incorporated in mRNA showed that the amount of mRNA was maintained stably over 100 minutes in the pyruvate-utilizing reaction whereas it decreased exponentially after a sharp, initial peak in the reaction using PEP (FIG. 5). The rapid decrease of mRNA content can be explained by the short half life of mRNA in the in vitro protein synthesis system. Due to the early depletion of energy source, the PEP system would not be able to produce new molecules of mRNA to balance the degradation. On the other hand, the continuous supply of ATP supports the sustained production of mRNA in the pyruvate system.

The generation of acetyl phosphate through this reaction cycle produces such by-products as carbon dioxide, acetate, and hydrogen peroxide. It was observed that the generation of these by-products did not significantly change the pH of the reaction buffer. Moreover, hydrogen peroxide, possibly the most serious by-product, does not seem to poison the system as suggested by the prolonged, constant rate of protein synthesis. Presumably, our reaction system contains enough endogenous catalase activity to avoid hydrogen peroxide toxicity. Addition of exogenous catalase to the reaction mixture did not affect either the rate or duration of protein synthesis.

Figure 6:
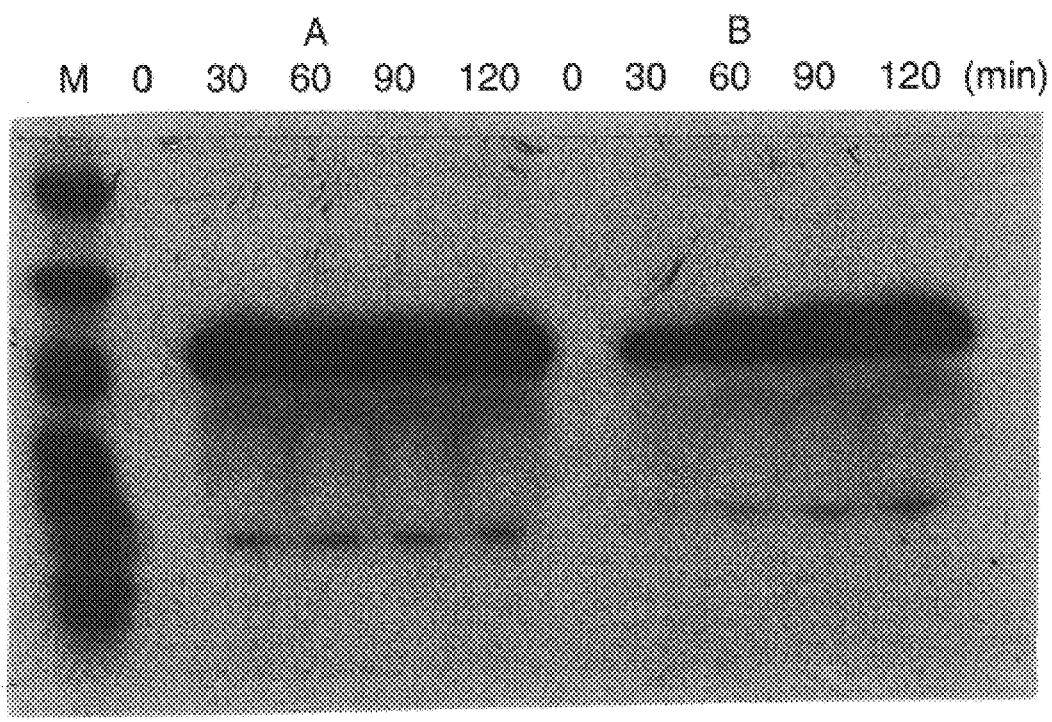
FIG. 6 is an SDS-PAGE analysis of in vitro synthesized CAT.

FIG. 6 shows the autoradiograph of samples taken from the PEP- and pyruvate-using reactions, respectively. This result indicates that in both systems, CAT is nearly the only protein synthesized. 5 μl samples of PEP (FIG. 6A) and pyruvate (FIG. 6B) system containing [$^{14}$C] leucine were withdrawn at given times and loaded on a gel. After running, the gel was dried and autoradiography was carried out.

Figure 7:
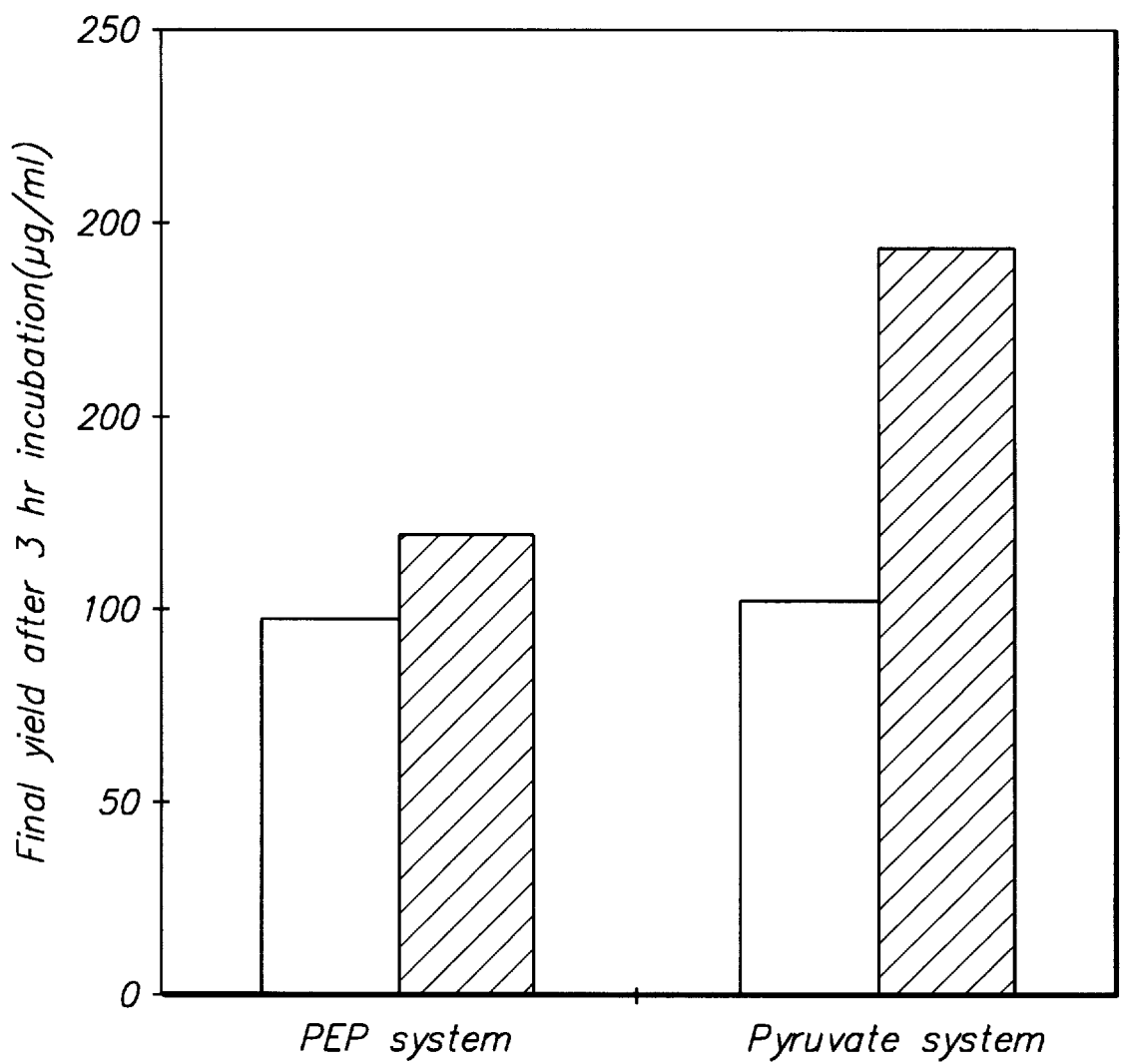
FIG. 7 shows the expression of proteins using PEP or pyruvate as energy sources.

Expression of human lymphotoxin in the new system. To further examine the potential of the new system, we applied it to the expression of human lymphotoxin. Unexpectedly, the expression level of lymphotoxin was much higher in the pyruvate system (150% as compared to the PEP system, see FIG. 7). Plasmid pK7CAT and pK7LT were used to produce CAT and LT in a standard PEP (blank column) system or in the new system using pyruvate (filled column). After examining the effect of inorganic phosphate and magnesium ion on the in vitro expression of human lymphotoxin, it was found that the expression level of this protein was more sensitive to changes in inorganic phosphate and magnesium concentrations than was CAT (FIG. 8).

Figure 8A:
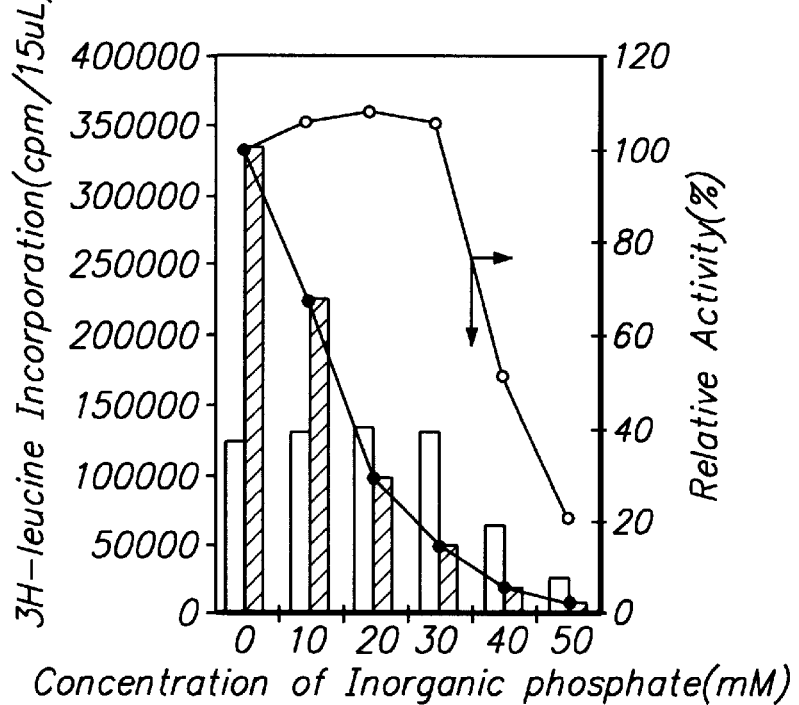
FIG. 8 is a graph depicting the different sensitivity of CAT and hLT production to the concentrations of exogenous inorganic phosphate and magnesium ion.
Figure 8B:
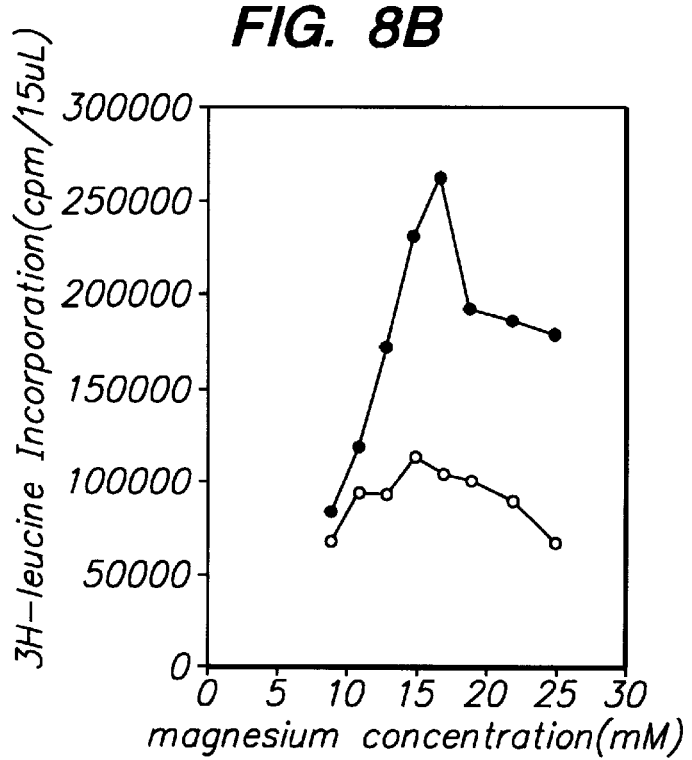

FIG. 8A, CAT and LT were produced using the PEP system with varying concentrations of Mg(OAc)$_2$; FIG. 8B, to the standard reaction mixture of PEP system, different concentration of exogenous inorganic phosphate were added and incubated for an hour. Open circles and columns, hLT; filled circles and columns, CAT. In other words, while the expression of CAT shows a relatively broad range of optimal magnesium concentration, slight changes of magnesium concentration dramatically affect the yield of hLT. Also, when different concentrations of exogenous inorganic phosphate were added to the reaction mixture, lymphotoxin synthesis was more vulnerable to excess inorganic phosphate.

The findings described here demonstrate that the coupling of the in situ generation of an energy source such as acetyl phosphate with the ATP regeneration reaction provides a steady supply of ATP for the protein synthesis reaction. This, in turn, allows the initial rate of protein synthesis to be maintained over greatly extended reaction periods. These results suggest that the early halt of protein synthesis experienced by conventional systems can be at least partly attributed to the degradation of ATP regenerating compounds.

Conventional batch in vitro protein synthesis systems require relatively high initial concentrations of PEP (around 30 mM) for maximal yield of protein synthesis. Such a high concentration will increase the rate and extent of non-productive degradation as it allows phosphatases with low affinities for PEP to bind and degrade the energy source. In contrast, the concentration of acetyl phosphate in the new system will not greatly exceed that of exogenously added inorganic phosphate (6.7 mM) although there may be marginal contribution of phosphate released from nucleotide triphosphates (1.2 mM ATP and 0.8 mM each of GTP, UTP and CTP). More than likely, the acetyl phosphate concentration will be much lower since its generation appears to be rate limiting and the reported Km value of acetate kinase for acetyl phosphate is 0.2 mM (Kessler and Knappe (1996) In *Esherichia coli* and Salmonella Cellular and Molecular Biology, Neidhardt et al, eds. American Society of Microbiology, Washington, D.C., pp. 199–205). Thus, a steady supply of acetyl phosphate, maintained at a rate limiting concentration, in our system is expected to improve the efficiency of high-energy phosphate bond utilization.

In addition to the depletion of ATP regeneration potential, degradation of PEP leads to a stoichiometric accumulation of inorganic phosphate, which can act as an inhibitor both on the transcription and translation reactions for protein synthesis through sequestration of essential magnesium ion from the reaction mixture.

By employing a method which recycles the inorganic phosphate ion, this problem was averted. In addition, as was shown with the expression of human lymphotoxin, our new system would be most advantageous for proteins whose expression is most sensitive to inorganic phosphate. This variable sensitivity to phosphate and magnesium concentration may also help to explain the need to determine the optimal magnesium concentration for each new protein. It is hoped the use of pyruvate as an energy source will allow more consistent performance from protein to protein.

Finally, this system enables us to easily control the rate of protein synthesis by adjusting pyruvate oxidase activity in the reaction mixture. This will provide a useful method to study various aspects of protein synthesis including protein folding as a function of the rate of protein synthesis.

Our subject system provides economic benefits. As is well known, the high cost of in vitro protein synthesis systems has been one of the obstacles preventing its use as a commercial method for protein production. Among the reaction components, the high energy phosphate bond compound contributes the largest fraction of cost. A calculation based on the reagent prices shows that PEP accounts for more than 70% of the total reagent cost. Probably, the cheapest source of commercially available ATP regenerating compound would be acetyl phosphate. However, since the cost for pyruvate is almost negligible compared to acetyl phosphate, not to mention PEP, this system will greatly reduce the cost of reagents for the cell-free production of proteins. Further, the cost for pyruvate oxidase can be eliminated by cloning it in the E.coli strain used for the preparation of S30 extract.

Through various efforts to enhance the initial rate of protein synthesis of our present system while maintaining the remarkably extended reaction period, a cell-free protein synthesis system of batch configuration may be developed, which enables economical, multiplexed production of families of bioactive proteins. In addition, such approaches can contribute to the development of new approaches for the economical, large scale production of commercial proteins.

EXAMPLE 3

Protein Synthesis with Repeated Addition of Energy Source

Figure 9A:
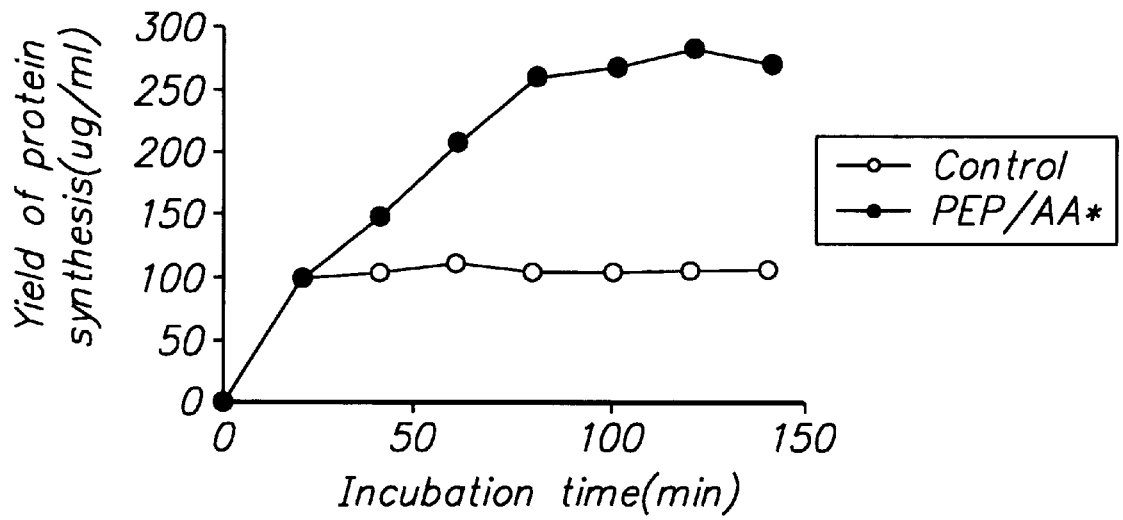
FIG. 9A and FIG. 9B depict the effect of repeated addition of the energy source.
Figure 9B:
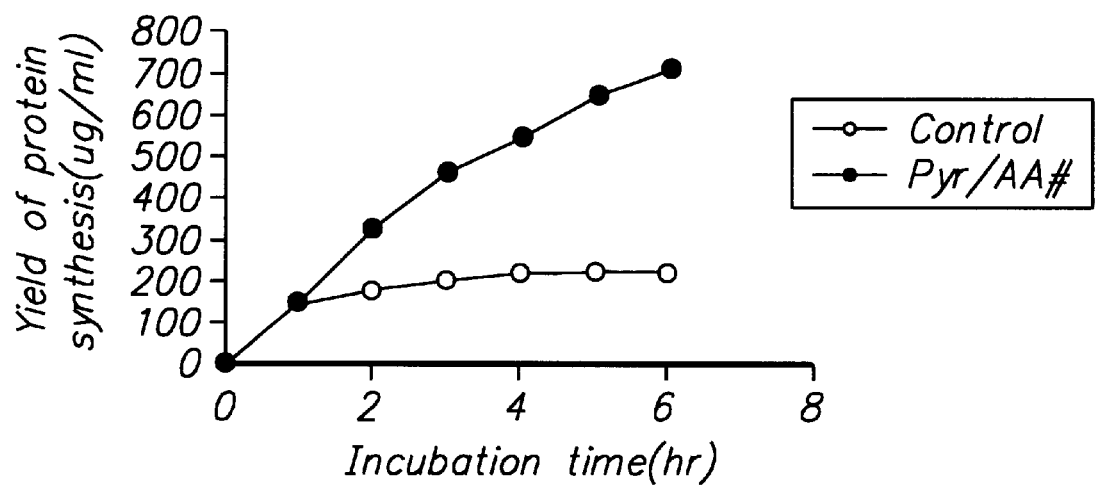

Synthetic reactions were set up as described in Example 1 and Example 2 for the synthesis of CAT, except that a mixture of PEP and amino acids was added every 20 min. to the PEP system; and a mixture of pyruvate and amino acids was added every hour to the pyruvate system. In both cases, the same concentration used initially was added each time. The results are shown in Table 1, and FIGS. 9A and 9B.

| | PEP system Yield of protein | | | Pyruvate system Yield of protein | |
|---|---|---|---|---|---|
| Incubation time(min) | synthesis (μg/ml**) | | Incubation time(hr) | synthesis (μg/ml**) | |
| | Control | PEP/AA* | | Control | Pyr/AA# |
| 0 | 0 | 0 | 0 | 0 | 0 |
| 20 | 98 | 100 | 1 | 142 | 150 |
| 40 | 102 | 147 | 2 | 176 | 327 |
| 60 | 110 | 206 | 3 | 201 | 461 |
| 80 | 102 | 259 | 4 | 219 | 545 |
| 100 | 102 | 266 | 5 | 223 | 648 |
| 120 | 104 | 281 | 6 | 219 | 706 |
| 140 | 104 | 268 | | | |

*Additions every 20 minutes
Additions every hour
**Yield per ml. of original reaction volume Clearly, the pyruvate system allows a much longer period of protein synthesis and much higher product yield than the PEP system. Not only is pyruvate much less expensive, the new system also can produce at least twice as much product when extended by repeated additions of amino acids and energy source.

What is claimed is:

1. A method for in vitro synthesis of biological macromolecules in a reaction mix, the method comprising:
   generating a compound containing a high energy phosphate bond from inorganic phosphate and a homeostatic energy source that lacks high energy phosphate bonds using an exogenous regenerative enzyme;
   generating ATP from said high energy phosphate bonds using a second exogenous enzyme or an endogenous enzyme; and
   synthesizing biological macromolecules in a reaction utilizing said ATP as an energy source;
   wherein exogenous enzymes are not intrinsic to said reaction mix and endogenous enzymes are intrinsic to said reaction mix.

2. The method of claim 1, wherein homeostatic secondary energy source is pyruvate and said regenerative enzyme is pyruvate oxidase.

3. The method of claim 2, wherein said pyruvate is present at an initial concentration of at least about 1 mM.

4. The method of claim 2, wherein said pyruvate is present at an initial concentration of at least about 10 mM.

5. The method of claim 2, wherein said pyruvate oxidase is present at an initial concentration of at least about 0.5 U/ml.

6. The method of claim 2, wherein homeostatic energy sources that result in accumulation of free phosphate are present at an initial concentration of less than about 1 mM.

7. The method of claim 1, wherein said synthesis of biological macromolecules comprises translation of mRNA to produce polypeptides.

8. The method of claim 7 wherein said synthesis also comprises transcription of mRNA from a DNA template.

9. The method of claim 1 wherein said synthesis of biological macromolecules is performed as a batch reaction.

10. The method of claim 1, wherein said synthesis of biological macromolecules is performed as a continuous reaction.

11. The method of claim 9 wherein repeated addition of said homeostatic energy source is performed during the synthesis.

12. The method according to claim 1, wherein said generating of a compound containing a high energy phosphate bond from inorganic phosphate and a homeostatic energy source that lacks high energy phosphate bonds is coupled with an oxidation reaction.

* * * * *